United States Patent
Rashidi et al.

(10) Patent No.: US 10,086,161 B1
(45) Date of Patent: Oct. 2, 2018

(54) RESPIRATORY APPARATUS AND METHOD FOR TREATING SLEEP APNEA

(71) Applicants: Majid Rashidi, Pepper Pike, OH (US); Geoffrey Sleeper, Bay Village, OH (US)

(72) Inventors: Majid Rashidi, Pepper Pike, OH (US); Geoffrey Sleeper, Bay Village, OH (US)

(73) Assignee: BRIGGS MEDICAL, LLC, Beachwood, OH (US)

( * ) Notice: Subject to any disclaimer, the term of this patent is extended or adjusted under 35 U.S.C. 154(b) by 594 days.

(21) Appl. No.: 14/847,708

(22) Filed: Sep. 8, 2015

Related U.S. Application Data

(60) Provisional application No. 62/046,436, filed on Sep. 5, 2014.

(51) Int. Cl.
*A62B 9/04* (2006.01)
*A61M 16/06* (2006.01)
*A61M 16/00* (2006.01)

(52) U.S. Cl.
CPC .... *A61M 16/0666* (2013.01); *A61M 16/0057* (2013.01); *A61M 16/0622* (2014.02); *A61M 16/0683* (2013.01)

(58) Field of Classification Search
CPC .......... A62B 9/02; A62B 9/022; A62B 9/025; A62B 9/027; F16K 15/14; F16K 15/144; F16K 15/147; F16K 15/16; A61M 16/0045; A61M 16/06; A61M 16/0666; A61M 16/0672; A61M 16/0677; A61M 16/0683; A61M 16/0688; A61M 16/0694; A61M 16/20; A61M 16/208; A61M 16/209; A61M 15/08; A61F 5/56
See application file for complete search history.

(56) References Cited

U.S. PATENT DOCUMENTS

| | | | |
|---|---|---|---|
| 2,833,306 A | 5/1958 | Cummings | |
| 4,134,424 A | 1/1979 | Zeyra et al. | |
| 4,239,038 A * | 12/1980 | Holmes | A61M 16/208 128/205.13 |
| 4,254,791 A | 3/1981 | Bron | |
| 4,642,833 A | 2/1987 | Stoltz et al. | |
| 6,478,026 B1 | 11/2002 | Wood | |
| 6,595,215 B2 | 7/2003 | Wood | |
| 6,626,179 B1 | 9/2003 | Pedley | |
| 6,722,360 B2 * | 4/2004 | Doshi | A61M 16/0488 128/200.24 |
| 6,776,162 B2 | 8/2004 | Wood | |
| 6,810,914 B2 | 11/2004 | Persson | |
| 7,244,235 B2 | 7/2007 | Bowman et al. | |
| 7,353,826 B2 | 4/2008 | Sleeper et al. | |

(Continued)

*Primary Examiner* — Joshua Lee
(74) *Attorney, Agent, or Firm* — Fay Sharpe LLP

(57) ABSTRACT

The Expiratory Positive Airway Pressure (EPAP) device disclosed herein fits at or around the a person's nose, and incorporates at least one bi-resistance air flow cartridge which allows air to enter the nose freely upon inspiration, while it produces a prescribed back pressure against the discharging air from the nose upon expiration. In a preferred embodiment, a pair of detachable bi-resistance air flow cartridges is attached to the underside of a frame, in alignment with two flexible nasal pillows that connect the device to a person's nostrils.

19 Claims, 10 Drawing Sheets

(56) References Cited

U.S. PATENT DOCUMENTS

| | | |
|---|---|---|
| 7,506,649 B2 | 3/2009 | Doshi et al. |
| 7,735,491 B2 | 6/2010 | Doshi et al. |
| 7,735,492 B2 | 6/2010 | Doshi et al. |
| 7,798,148 B2 | 9/2010 | Doshi et al. |
| 7,856,979 B2 | 12/2010 | Doshi et al. |
| 7,992,564 B2 | 8/2011 | Doshi et al. |
| 8,061,357 B2 | 11/2011 | Pierce et al. |
| 8,215,308 B2 | 7/2012 | Doshi et al. |
| 8,235,046 B2 | 8/2012 | Doshi et al. |
| 8,291,909 B2 | 10/2012 | Doshi et al. |
| 8,302,606 B2 | 11/2012 | Doshi et al. |
| 8,302,607 B2 | 11/2012 | Pierce et al. |
| 8,365,731 B2 | 2/2013 | Ho et al. |
| 8,365,736 B2 | 2/2013 | Doshi et al. |
| 9,086,160 B2 * | 7/2015 | Harper .................. F16K 15/144 |
| 9,138,553 B2 * | 9/2015 | Wood .................. A61M 16/0666 |
| 9,393,375 B2 * | 7/2016 | Hernandez ............ A61M 16/06 |
| 9,615,962 B2 * | 4/2017 | Robitaille .................. A61F 5/56 |
| 9,833,354 B2 * | 12/2017 | Loomas .................. A61F 5/56 |
| 2006/0144398 A1 * | 7/2006 | Doshi .................. A61M 15/08 |
| | | 128/204.23 |
| 2007/0283962 A1 | 12/2007 | Doshi et al. |
| 2007/0295338 A1 * | 12/2007 | Loomas ................ A61M 15/08 |
| | | 128/207.18 |
| 2009/0050144 A1 | 2/2009 | Pierce et al. |
| 2009/0145441 A1 | 6/2009 | Doshi et al. |
| 2009/0194100 A1 | 8/2009 | Minagi |
| 2009/0308398 A1 | 12/2009 | Ferdinand et al. |
| 2009/0308402 A1 * | 12/2009 | Robitaille .................. A61F 5/56 |
| | | 128/848 |
| 2011/0067709 A1 | 3/2011 | Doshi et al. |
| 2011/0211974 A1 * | 9/2011 | Harper .................. F04B 53/106 |
| | | 417/53 |
| 2011/0218451 A1 | 9/2011 | Lai et al. |
| 2011/0220123 A1 | 9/2011 | Robson |
| 2011/0240038 A1 | 10/2011 | Doshi et al. |
| 2012/0285470 A9 | 11/2012 | Sather et al. |
| 2013/0000647 A1 | 1/2013 | Holley et al. |
| 2013/0081637 A1 | 4/2013 | Foley et al. |
| 2014/0034064 A1 | 2/2014 | Chen et al. |
| 2014/0128761 A1 | 5/2014 | Cline et al. |
| 2014/0150801 A1 * | 6/2014 | Rusher .................. A63B 23/18 |
| | | 128/207.16 |
| 2015/0202404 A1 * | 7/2015 | Patriksson ............... A62B 9/02 |
| | | 128/202.22 |
| 2016/0051791 A1 * | 2/2016 | Ewers ............... A61M 16/0666 |
| | | 128/204.23 |
| 2018/0085246 A1 * | 3/2018 | Loomas ............... A61M 15/002 |

* cited by examiner

RESPIRATORY APPARATUS AND METHOD FOR TREATING SLEEP APNEA

This application claims the priority benefit of U.S. provisional application Ser. No. 62/046,436, filed Sep. 5, 2014, the entire disclosure of which is expressly incorporated herein by reference.

FIELD OF THE DISCLOSURE

The present disclosure relates generally to an expiratory positive airway pressure (EPAP) device, and more particularly, to a nasal interface with integrated bi-resistance air flow cartridges.

BACKGROUND

Sleep apnea is a potentially life-threatening breathing disorder characterized by brief interruptions of breathing during sleep. There are two types of sleep apnea; central and obstructive. Central sleep apnea, which is less common, occurs when the brain fails to send appropriate signals to breathing muscles to initiate ventilation. Obstructive sleep apnea (OSA) occurs when air cannot flow into or out of the person's nose or mouth although the efforts to breathe continue. In a given night, the number of involuntary breathing pauses as measured by the Apnea-Hypopnea Index (AHI) may exceed 30, which is considered to be severe OSA. Early recognition and treatment of sleep apnea is important because it may be associated with irregular heartbeat, high blood pressure, heart attack, stroke and other co-morbid medical conditions. The estimated prevalence of OSA is 2% of women and 4% of men between the ages of 40-65. It is estimated that up to 80% of patients remain undiagnosed.

Continuous Positive Airway Pressure (CPAP) therapy is the gold standard for the treatment of OSA. However, despite the known efficacy of CPAP therapy, it is estimated that 46-83% of patients are nonadherent.

Nasal Expiratory Positive Airway Pressure (EPAP) is a viable FDA approved treatment of OSA. EPAP is effective in reducing AHI and improving subjective daytime sleepiness. It has been shown to improve tolerability and long term compliance.

A currently approved and marketed EPAP device consists of a pair of valves fixed to the nares with adhesive disks. The valves are disposable and are approved for one night of use only. The cost of continuous replacement, as well as some complaints of irritation caused by the adhesive, has limited the use of this therapy.

Further, some have complained of some restriction to inspiration because of the small surface area of the flap valve.

SUMMARY

The following presents a simplified summary of the present disclosure in order to provide a basic understanding of some aspect of the disclosure. This summary is not an extensive overview of the disclosure, but rather its purpose is to present some concepts thereof in a simplified form as a prelude to the more detailed description that is presented later.

The present disclosure relates to a pair of bi-resistance air flow cartridges and a pair of nasal pillows to administer expiratory positive airway pressure (EPAP) therapy. According to a first aspect of the present disclosure, a pair of bi-resistance air flow cartridges, each comprised of a cylinder and a flexible thin-walled member or shell, is aligned in series with a pair of nasal pillows to allow unimpeded inspiration and restricted expiration to create back pressure. The nasal pillows and cartridges are held in alignment with a frame, and the device is held in place on the patient by headgear straps.

According to another aspect of the present disclosure, EPAP is created by a pair of bi-resistance air flow cartridges, each comprised of a cylinder and flexible thin-walled shell. The flexible thin-walled shell is open at one end, and is at least partially attached to the lumen of the cylinder along an axis. A concave channel extends essentially the length of the flexible thin-walled shell on an axis generally opposite the axis of attachment. The flexible thin-walled shell is open on the end nearest the nares, which allows the shell to expand on expiration. The flexible thin-walled shell seals the lumen of the cylinder during expiration except for the area created by the channel, thus creating back pressure. The flexible thin-walled shell collapses or caves in completely on inspiration, allowing unimpeded airflow.

According to yet another aspect of the present disclosure, an EPAP device includes a pair of detachable bi-resistance air flow cartridges in series with a respective pair of detachable nasal pillows held in alignment with a housing or frame. This assembled device is held in proper position on the patient by a headgear strap. EPAP is created when a flexible thin-walled shell inside each cartridge expands to seal a perimeter or inner circumference of a lumen of the cylinder, except for a concave channel integrated into the flexible thin-walled shell, thus restricting expiration to the area of the channel. Unimpeded inspiration occurs because the flexible thin-walled shell collapses.

According to yet another aspect of the present disclosure, a method of manufacturing an EPAP device is provided. The device is an assembly of at least one, and in a preferred arrangement, two bi-resistance air flow cartridges which attach to a frame. The cartridges are replaceable, and are easily attached and detached from the frame. The nasal pillows are preferably located on an opposite side of the frame, and are also replaceable, and the nasal pillows are likewise easily attached and detached from the frame. Integrated to frame is a headgear assembly for securing the device to a user. In one example, the headgear assembly includes a strap assembly that has first and second portions secured to opposite ends of the frame, and free ends of the first and second strap portions secured to each other. Slots may be provided in the opposite ends of the frame and each slot receives a respective headgear strap portion and the free ends of the first and second strap portions use hook and loop material to selectively and adjustable secure the strap portions together, and secure the device to the user.

The following description and the annexed drawings set forth, in detail, certain illustrative aspects of the disclosure. These aspects are indicative, however, of but a few of the various ways in which the principles of the disclosure may be employed and the present disclosure is intended to include all such aspects and their equivalents. Other advantages and novel features of the disclosure will become apparent from the following detailed description of the disclosure when considered in conjunction with the drawings.

DETAILED DESCRIPTION OF THE DISCLOSURE

Figure 1:
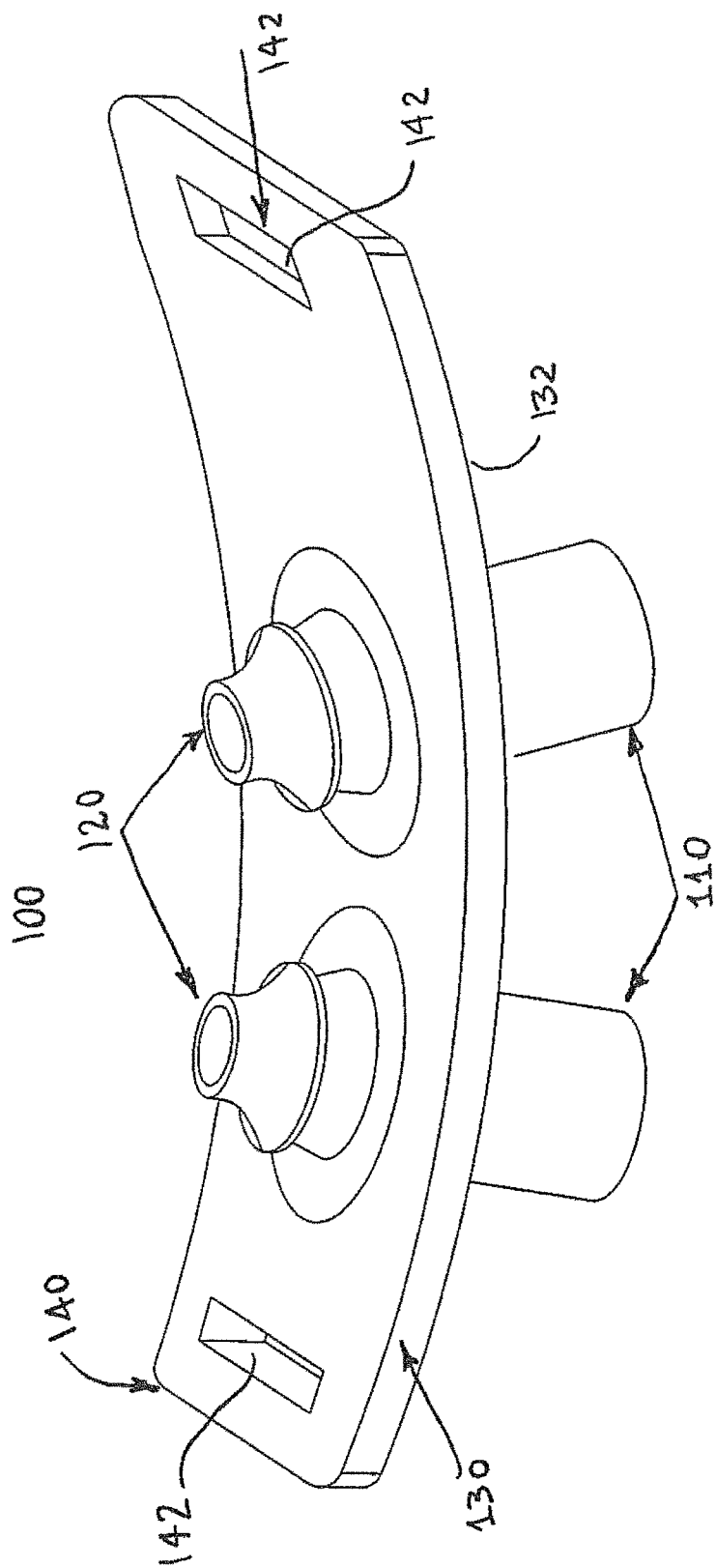
FIG. 1 illustrates a perspective view of the EPAP device in accordance with an aspect of the present disclosure.

The present disclosure provides an EPAP device having one or a pair of bi-resistance air flow cartridges in series with a pair of nasal pillows. The present disclosure will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the reading of the drawings. In the following description, for purposes of explanation, numerous specific details are set forth in order to provide a thorough understanding of the present disclosure. It may be evident, however, that the present disclosure may be practiced without some of these specific details.

Turning initially to FIG. 1, an example of an EPAP device 100 in accordance with a first aspect of the present disclosure is illustrated. The EPAP device 100 comprises a pair of bi-resistance air flow cartridges 110 and a pair of nasal pillows 120, which attach to a housing or frame 130. Preferably the air flow cartridges 110 and the nasal pillows 120 are easily attached and detached to the frame 130 via mechanical connections such as snap fit connections that allow easy replacement of one or more of these components of the assembly, and still assure a secure sealed connection with the frame for use by a patient. The air flow cartridges 110 are in fluid communication with the nasal pillows 120, i.e., each air flow cartridge is typically in air flow communication with a respective nasal pillow, so that air can flow along an air path from respective nostrils of a user or patient (not shown), through the nasal pillow, through the housing 130, and through the cartridges. Here, the frame 130 has a thin elongated conformation with the air flow cartridges 110 extending from a first or outer face 132 of the frame (i.e., that face outwardly from the user) while the nasal pillows extend outwardly from a second or inner face 134 of the frame (i.e., that face inwardly toward the user). The EPAP device 100 is held in place by a headgear strap (not shown) with hook and loop material, for example, that attaches to headgear strap flanges 140, which are coupled to the frame 130 or integrally formed in first and second opposite ends of the frame, to facilitate utilization of a headgear strap (not shown). Each of the headgear strap flanges 140 includes at least one aperture, slot, or opening 142 for receiving a portion of the headgear strap therethrough. When the nasal pillows 120 of the EPAP device 100 are inserted into the nares of the patient in a manner generally known in the art, the headgear strap securing the EPAP device 100 provides both a backward pressure, as well as an angular, upward pressure, creating a desired seal around the nares. For sleep apnea therapy, the EPAP device 100 must produce expiratory pressures somewhere between seven (7) and twelve (12) cm $H_2O$, also more generally referred to herein as clinically indicated positive airway pressure.

Figure 2:
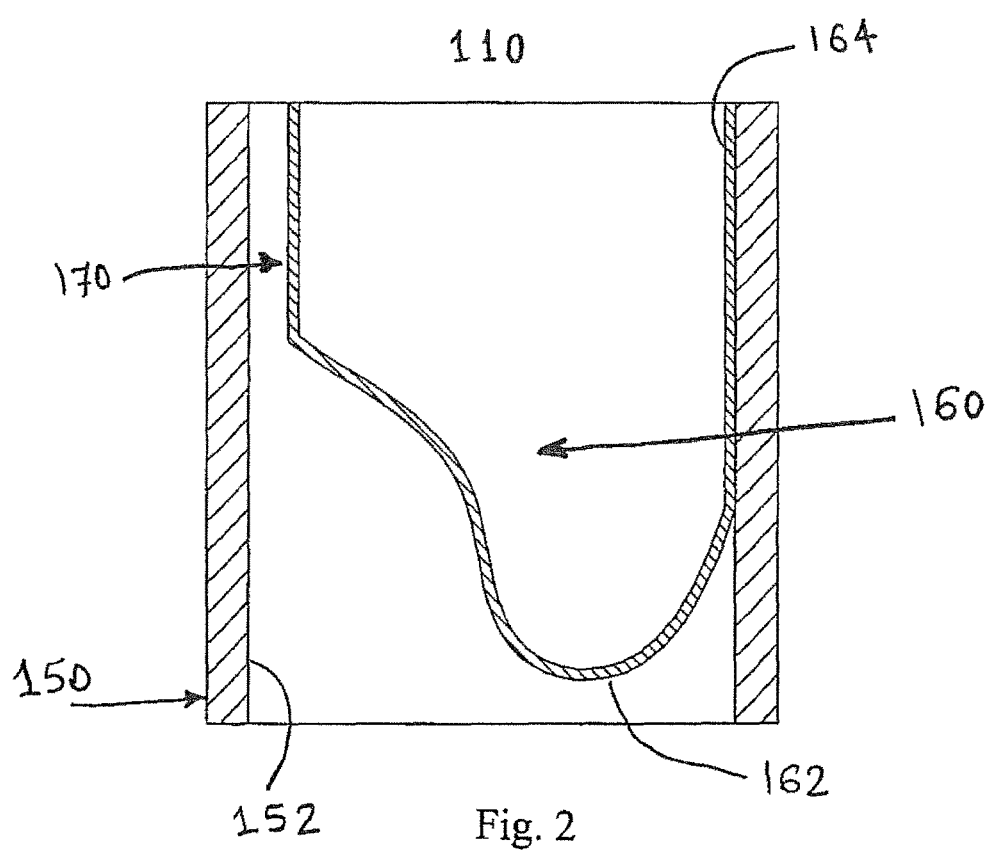
FIG. 2 illustrates a front cut-away view of the bi-resistance air flow cartridge.

FIG. 2 illustrates internal structure of one of the bi-resistance air flow cartridges 110. The cartridge 110 comprises a lumen or cylinder 150 and an flexible thin-walled shell 160 which has an integrally molded concave channel 170. The flexible thin-walled shell 160 is secured or joined at least in part to an inner perimeter or circumference 152 of the lumen 150 as shown and described in greater detail in FIGS. 3-4. Each cartridge 110 includes a member having a longitudinally extended lumen 150, preferably in the form of a cylinder, and the flexible thin-walled shell 160 which is formed as an elongated thin-walled shell, with one end 162 closed, and the other end 164 open.

A portion of the exterior surface of the flexible thin-walled shell 160, extending along its longitudinal axis, is secured to the interior lumen 150, creating a partial attachment between the flexible thin-walled shell and the lumen in the cartridge 110. For example, it is contemplated that the flexible thin-walled shell 160 is secured along substantially an entire axial length thereof to the inner surface of the lumen 150 (e.g., along the right-hand edge as illustrated in FIG. 2) and is secured over an arcuate extent (shown in FIG. 4 as being secured over approximately 180 degrees of the inner surface of the lumen). The remainder of the outer surface of the flexible thin-walled shell 160 is detached and free to conform/deflate dues to its thin-walled, flexible structure. The flexible thin-walled shell 160 can be secured in any well-known manner, for example, a mechanical attachment such as a clip could be used, or an adhesive arrangement such as a double-sided adhesive tape can be used to secure the flexible thin-walled shell to the inner surface of the lumen 150. The flexible thin-walled shell 160 could also be fused to the lumen where the materials permit such a mechanical connection. In one embodiment of the device 100, a longitudinal groove 170 is formed on the wall thickness of the lumen 150 of the cartridge that is positioned on the side of the flexible thin-walled shell 160 which is not secured to the lumen.

Figure 3:
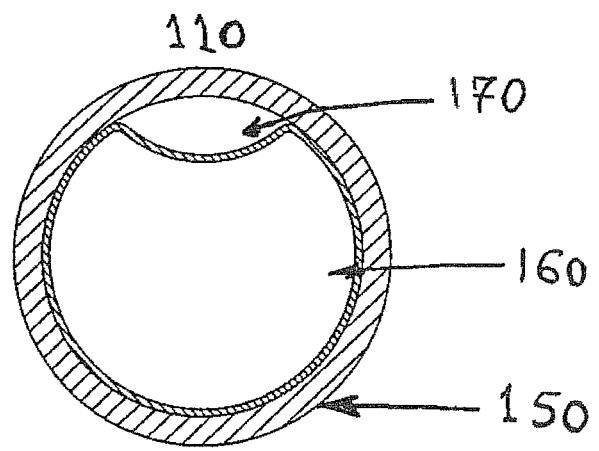
FIG. 3 illustrates a top view of the cartridge during exhalation, with the flexible thin-walled shell expanded.

FIG. 3 depicts a view of the bi-resistance air flow cartridge 110, with the flexible thin-walled shell 160 fully expanded during expiration where the flexible thin-walled shell is expanded and extends around substantially the entire inner perimeter of the lumen 150 (i.e., flow outward from the patient through openings in the pillows 120, through the frame 130, and outwardly through the lumen 150 of the cartridge 110 wherein the flexible thin-walled shell 160 is inflated and reduces the cross-sectional area through which air can flow (downwardly as shown in FIG. 2)). The reduced area which creates back pressure during expiration is formed by the flexible thin-walled shell channel 170 and the lumen of the cylinder 150.

Figure 4:
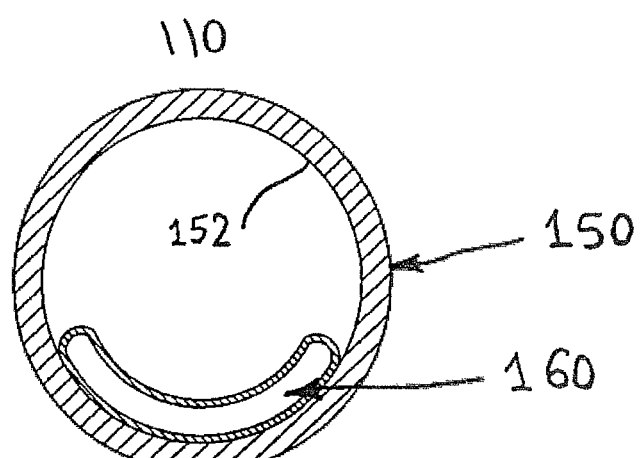
FIG. 4 illustrates a top view of the cartridge during inspiration, with the flexible thin-walled shell collapsed.

FIG. 4 depicts a view of the bi-resistance air flow cartridge 110, with the flexible thin-walled shell 160 fully collapsed during inspiration (shown collapsed along the lower portion of the inner perimeter of the lumen of the cartridge assembly). This position of the flexible thin-walled shell 160 allows inspiration to occur without added resistance since substantially an entirety of the cross-sectional area of the lumen is open or unrestricted (FIG. 4) versus substantially an entirety of the cross-sectional area of the lumen being closed or restricted (FIG. 3) except along the flexible thin-walled shell channel 170.

Figure 5:
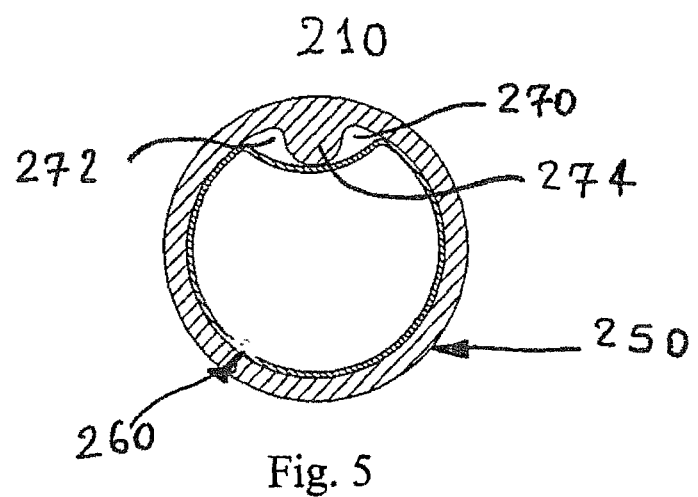
FIG. 5 illustrates a top view of another cartridge during exhalation, with the flexible thin-walled shell expanded.

FIG. 5 depicts a view of another bi-resistance air flow cartridge 210, with the flexible thin-walled shell 260 fully expanded during expiration. The reduced area which creates back pressure during expiration is formed by a protrusion or rail 270 integrally formed (e.g., molded) to the lumen of the cylinder 250 and extends inwardly into the cross-sectional opening of the hollow lumen and the rail deflects a portion of the flexible thin-walled shell 260. Here, the rail 270 has a generally mushroom-shape where an undercut or necked down region 272 interconnects an enlarged head portion 274, with the inner perimeter of the lumen. The head portion 274, for example, extends generally radially inward into the hollow, cross-sectional area of the lumen 250 and the undercut region 272 assures a flow path around the flexible thin-walled shell.

Figure 6:
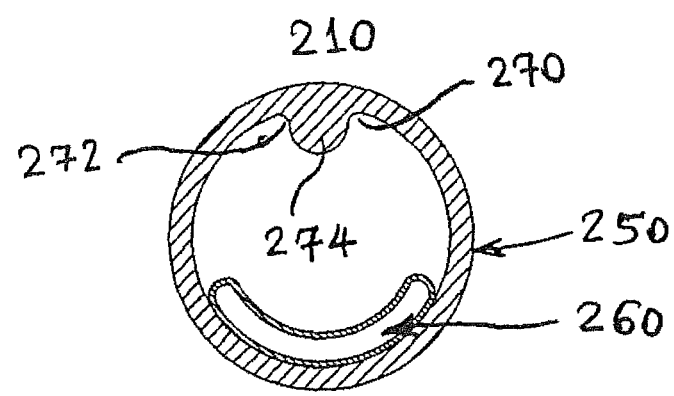
FIG. 6 illustrates a top view of another cartridge during inspiration, with the flexible thin-walled shell collapsed.
Figure 7:
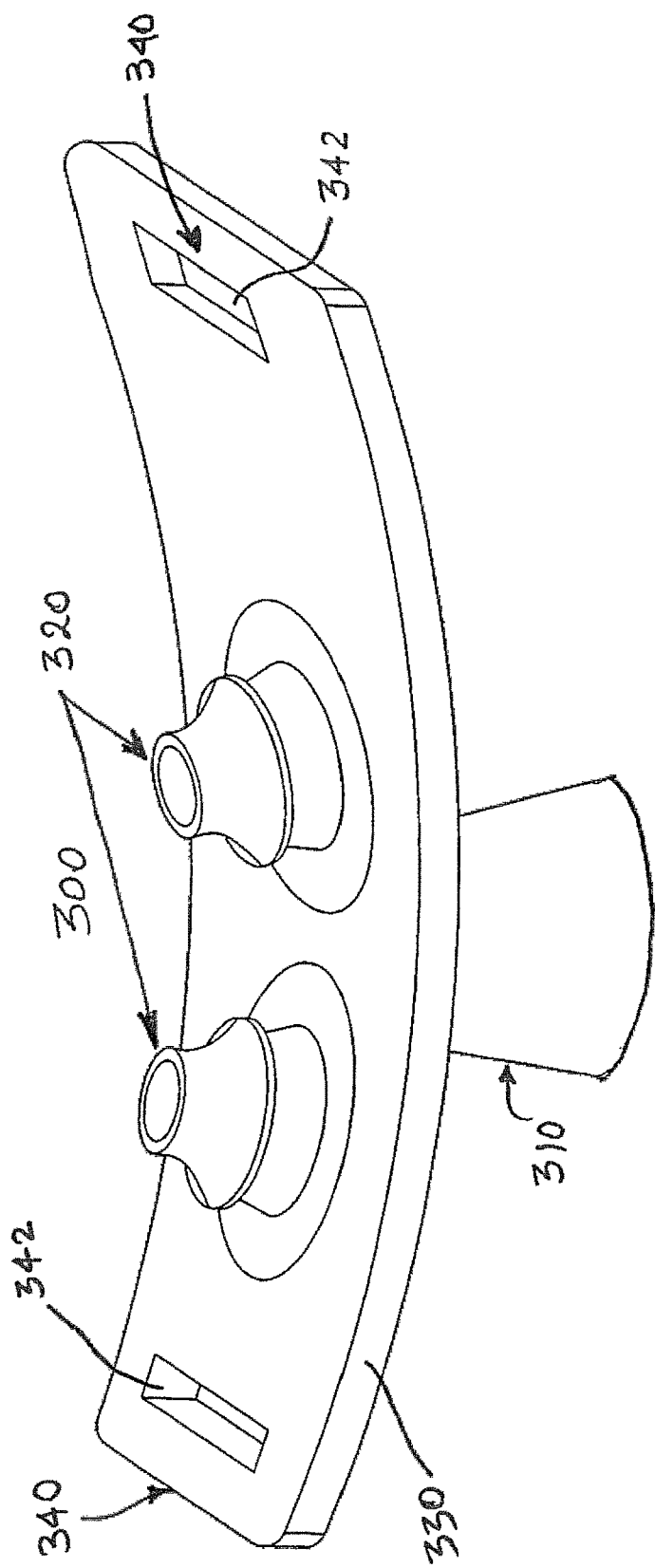
FIG. 7 illustrates a perspective view of another EPAP device that has some similar attributes to the device of FIG. 1 but uses only a single air flow cartridge that communicates with the nasal pillows.

FIG. 6 depicts a view of the bi-resistance air flow cartridge 210 of FIG. 5, with the flexible thin-walled shell 260 fully collapsed during inspiration. This position of the flexible thin-walled shell 260 allows inspiration to occur without added resistance. As is evident in FIG. 6, the interior, hollow cross-sectional area of the lumen 250 is open or unrestricted (FIG. 6) when compared with a substantial entirety of the cross-sectional area of the lumen being closed or restricted (FIG. 5) except along the rail 270, FIG. 7 illustrates an alternate example of an EPAP device 300 in accordance with another aspect of the present disclosure. The EPAP device 300 comprises a single bi-resistance air flow cartridge 310 and a pair of nasal pillows 120, which attach to a frame 330. The EPAP device 300 is held in place, for example, by a headgear strap (not shown) with hook and loop material or other suitable strap connection that attaches to the headgear strap flanges 340, which are coupled or integrated into opposite ends of the frame 330, to facilitate utilization of a headgear strap (not shown). Each of the headgear strap flanges 340 includes at least one aperture 342 for receiving a portion of the headgear strap portions therethrough. When the nasal pillows 320 of the EPAP device 300 are inserted into the nares of the patient (not shown), the headgear strap securing the EPAP device 300 provides both a backward pressure as well as an angular, upward pressure, creating a seal around the nares. The single air flow cartridge 310 may adopt either of the previously described versions (FIGS. 2-4 or FIGS. 5-6) or still other arrangements to be described below or that fall within the general concept to be described below and/or as claimed. The single air flow cartridge 310 provides air flow to each of the nasal pillows 320. Further, the remainder of the frame 330, the interconnection of the air flow cartridge 210, and nasal pillows 320 to the frame, and the inclusion of a headgear strap (not shown) preferably secured at opposite ends of the frame, are substantially the same as shown and described above in connection with the earlier embodiments.

Figure 8:
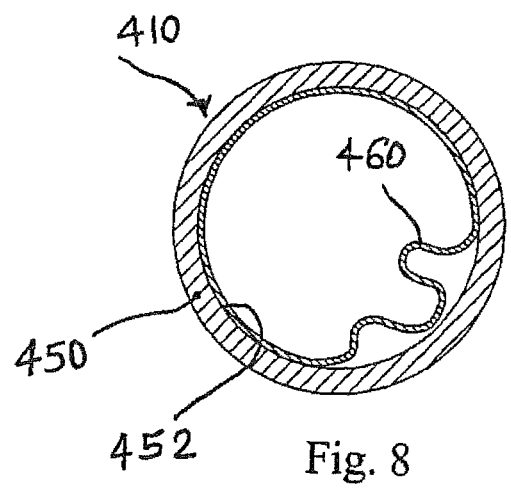
FIG. 8 illustrates a front cut-away view of another bi-resistance air flow cartridge where the flexible thin-walled shell has a substantially greater perimeter dimension than an inner perimeter dimension of a lumen to which the flexible thin-walled shell is secured.

FIG. 8 illustrates a slightly modified embodiment of the air cartridge 410, and particularly a modified flexible thin-walled shell 460 that has a substantially greater peripheral dimension than an inner perimeter 452 of the lumen (housing cylinder) 450. As a result of the larger dimension, the flexible thin-walled shell 460 does not form a smooth, complete perimeter seal with the inner perimeter 452 of the lumen 450, and air can always flow past the flexible thin-walled shell in a reduced amount during expiration (as shown). Of course during inspiration, the flexible thin-walled shell 460 collapses and allows a free flow of air through the bi-resistance air flow cartridge 410. The cartridge 410 includes at least one cylinder 450 and the expandable, flexible thin-walled shell 4360 is preferably secured to the lumen along a portion of the lumen inner perimeter.

Figure 9:
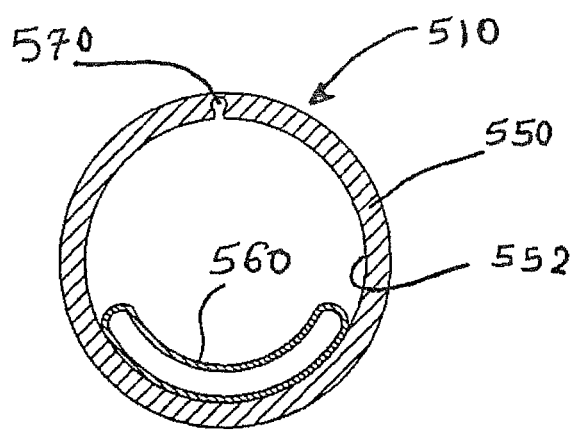
FIG. 9 illustrates a top view of another cartridge during exhalation, with the flexible thin-walled shell expanded and a recess extends outwardly into the lumen wall to allow air flow therepast in the expanded flexible thin-walled shell condition.

FIG. 9 depicts a view of the bi-resistance air flow cartridge 510, with the flexible thin-walled shell 560 fully expanded during expiration. A reduced cross-sectional area is formed by a passage that extends generally radially outward from an inner perimeter of the lumen 560 to define a passage 570 of limited cross-sectional area which creates back pressure during expiration since the flexible thin-walled shell expands to seal along a remainder of the inner perimeter of the lumen. The passage 570 can adopt a wide array of configurations and is preferably located so that the flexible thin-walled shell 560 does not inadvertently seal over the passage during expiration. During inspiration, the flexible thin-walled shell collapses in the same manner as described above.

Figure 10:
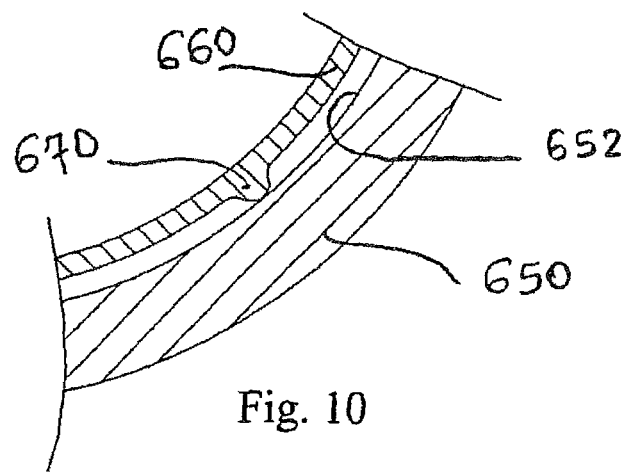
FIG. 10 illustrates a top view of another cartridge during expiration, with the flexible thin-walled shell expanded and prevented from completely sealing with an inner perimeter of the lumen by providing a rib on the flexible thin-walled shell.

FIG. 10 depicts an enlarged view of flexible thin-walled shell 660 shown expanded during expiration but unable to form a complete seal around the entire inner perimeter of the lumen 660 because of the provision of a rib 670 that is integrated into the flexible thin-walled shell.

Figure 11:
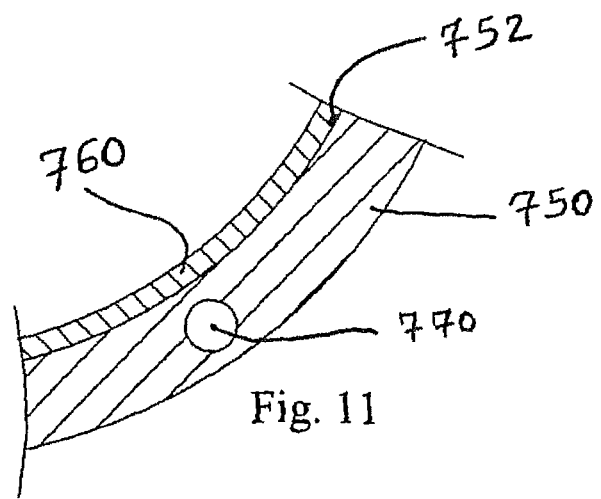
FIG. 11 illustrates an enlarged view of a wall portion of the lumen of yet another cartridge embodiment.

FIG. 11 depicts another design of a passage 770 formed in the wall of the lumen or cylinder 750. Even when the flexible thin-walled shell 760 is fully expanded as shown in the view of the bi-resistance air flow cartridge 710, a reduced area is provided in the wall of the lumen 750 which creates back pressure during expiration. The passage 770 is shown in cross-section, although it will be understood that the passage communicates with the interior of the lumen at axially spaced locations upstream and downstream of the flexible thin-walled shell so that air can always flow therethrough even when the flexible thin-walled shell is fully expanded during expiration.

Figure 12:
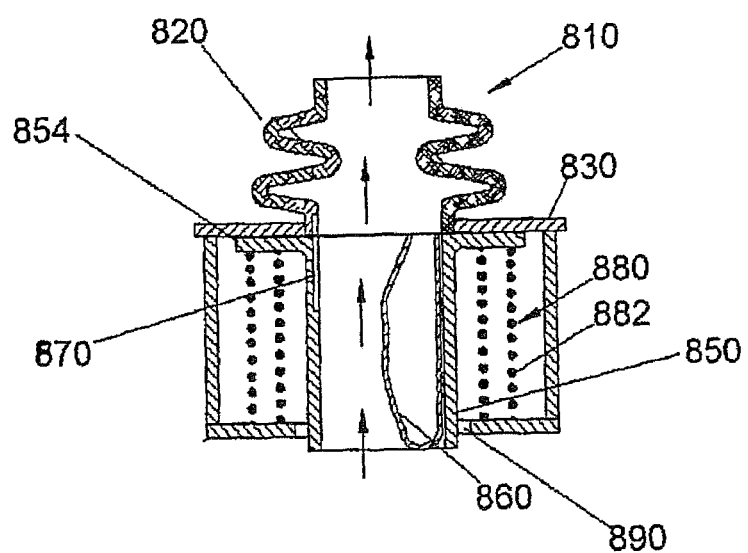
FIG. 12-14 illustrate longitudinal cross-sectional views through another embodiment of an EPAP device showing different states of operation.
Figure 13:
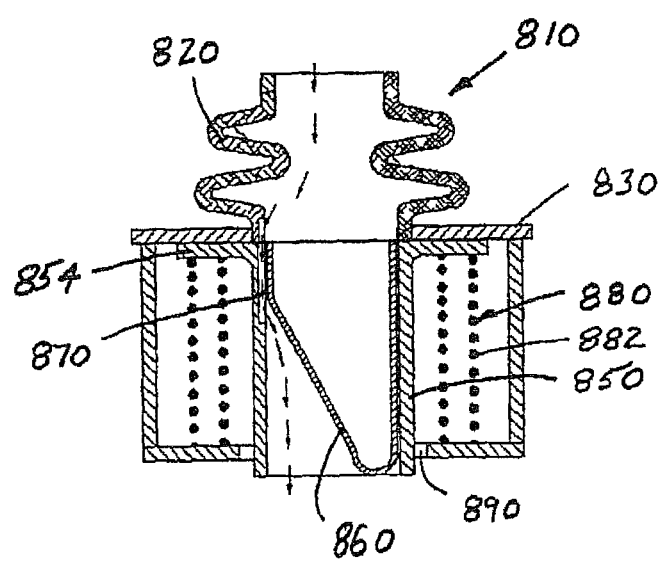
Figure 14:
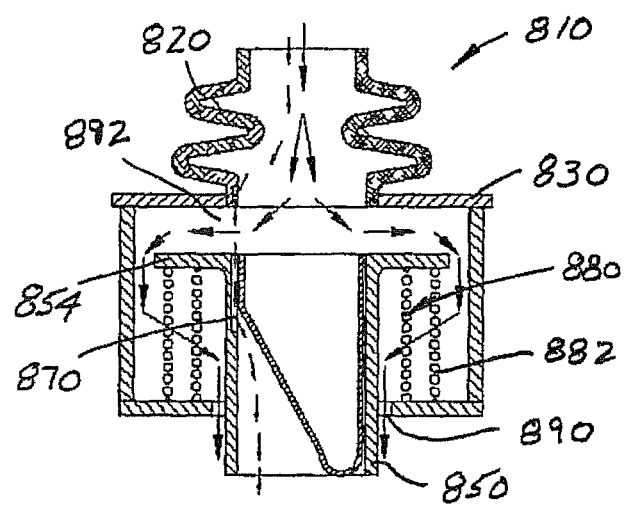

FIG. 12-14 depict a cross-sectional view of another bi-resistance air flow cartridge 810, with the flexible thin-walled shell 860 represented as collapsed in FIG. 12 to provide no resistance to air flow in the inhalation or inspiration phase (air flows past the collapsed flexible thin-walled shell as shown by the arrows), and fully expanded during normal expiration or exhalation as shown in FIG. 13 where a more limited amount of air flows as shown by the arrows through passage 870. The air flow cartridge 810 includes a flexible thin-walled shell 860 that is secured to the lumen 850 (again, along a substantial entire inner perimeter of the lumen). The lumen 850 is modified to include a flange 854 that cooperates with the frame 830. The lumen 850 in this embodiment is not stationary relative to the flange (as in the prior embodiments) but instead is capable of potential limited movement relative to the frame 830 (compare FIGS. 12 and 13 with FIG. 14). More specifically, the flange 854 of lumen 850 is urged into sealing engagement against the frame 830 by a biasing member 880. In the illustrated arrangement of FIG. 12, the biasing member 880 is a coil spring assembly 882, although still other springs (e.g. flat or wave springs) or biasing structures that urge the lumen flange 854 into selective sealing engagement with the frame 830 are contemplated without departing from the scope and intent of the present disclosure. If the pressure during expiration exceeds a predetermined level (upper threshold), the force of the biasing member 880 is overcome and the flange 854 and frame 830 separate (FIG. 14). This will cause expiration air flow through a gap 892 between the flange 854 and frame 830, around the biasing member 880, and through passage 890 so that further build-up of resistance to expiration air flow is prevented (and air flow can also continue through the passage 870 as represented by the arrows representing air flow). Once the expiration pressure is reduced, the force imposed by the biasing member overcomes the countering force and again urges the flange 854 into sealing engagement with the frame 830.

In summary, an expiratory positive airway pressure (EPAP) device includes at least one bi-resistance air flow cartridge which allows air to enter the nose freely upon inspiration, but produces a prescribed back pressure during the expiration phase of breathing by reducing the cross-sectional area of the air flow path. In the EPAP device, the cartridge includes a member having a lumen and an flexible thin-walled shell that has one end closed and one end open. The flexible thin-walled shell is secured to the lumen of the said member over a portion of the exterior surface of the flexible thin-walled shell. The flexible thin-walled shell is open on one end. The cartridge has a longitudinally extended groove in its wall thickness that is adjacent to the un-secured portion of the flexible thin-walled shell to the cartridge. The flexible thin-walled shell has an integral longitudinally extending rib that is adjacent to the un-secured portion of the flexible thin-walled shell to the cartridge. The cartridge is aligned so that the open end of the flexible thin-walled shell is closest to the patient's nares. The flexible thin-walled shell expands upon expiration. The expanded flexible thin-walled shell forms a partial seal around the lumen of the cartridge except for the area created by the groove formed in the wall thickness of the cartridge. The therapeutic resistive pressure is created by the fluidic resistance of expiring path through the restricted cross-sectional area formed by the expanded flexible thin-walled shell and the groove of the cartridge. The therapeutic pressure ranges from 7 to 12 cmH2O. The flexible thin-walled shell collapses against the lumen on inspiration. The collapsed flexible thin-walled shell causes no fluidic resistance against inspiration. The cartridges and nasal pillows easily attach and detach from a housing or frame. The cartridges are aligned in series with the pillows along the path of the patient's natural breathing. The device uses at least one nasal pillow to create a comfortable interlace between the frame and the patient's nares. The device is held in position under the patient's nose by means of a headgear strap. The device is reusable, with the pillows, cartridges and headgear intended to be replaceable to prolong the useful life of the device.

It is believed that other commercially available EPAP devices that provide a one-way valve are either hinged or use a ball valve to restrict flow. The mechanism of action of the present disclosure uses a flexible thin-walled shell that expands and collapses to provide no resistance during inspiration and provide a desired limited level of resistance during expiration.

The above-described EPAP device also has other potential medical applications. For example, the device can be used as an Overnight Nasal EPAP to treat Obstructive Sleep Apnea (OSA) or Disruptive Snoring by preventing upper airway narrowing and collapse. The nasal EPAP alleviates the upper airway obstruction, which occurs repeatedly during sleep in OSA, by acting as "a pneumatic stent". Prevention of such collapse also prevents the resulting swings in blood pressure, heart rate, micro-arousals, sleep disruption, and autonomic vacillation. If untreated, these phenomena can lead to hypertension, stroke, heart attack, heart failure, diabetes, metabolic syndrome, etc.

Nasal EPAP may decrease the anesthetic, sedative, and post-operative complications resulting from previously-untreated OSA (known or suspected OSA). Due to Nasal EPAP simplicity, tolerance, & cost advantages, it can be used in place of CPAP. By using it nightly for the month prior to surgery, general anesthesia, & even conscious sedation for out-patient endoscopies, the increased risk of untreated OSA can be removed. Also, continuing EPAP into the postoperative period can replace CPAP. Lower resistance levels of nasal EPAP can be used during sleep, to eliminate disruptive snoring, even in those without sleep apnea.

Another use of the device is as a Daytime Nasal EPAP, to prevent atelectasis & pneumonia, postoperatively and in chronic restrictive lung disorders, by increasing functional residual volume (FRC). Because nasal EPAP increases functional residual volume (FRC) and produces mild lung hyperinflation, it can also prevent postoperative atelectasis, hypoxemia, hypoventilation, and pneumonia. It can replace the non-compliance of incentive spirometry and the time and cost-intensive measures such as CPAP, nebulizer therapy, and chest physical therapy.

Besides nasal EPAP use in the postoperative setting, it can produce these benefits in chronic restrictive respiratory disorders. Examples include neuromuscular diseases like muscular dystrophy, other myopathies, diaphragmatic weakness, kyphoscoliosis. Other groups who might benefit include morbid obesity, ascites, pregnancy, and middle lobe syndrome. It potentially could obviate or delay the need for chronic BIPAP therapy in the more severe patients.

The nasal EPAP can also be used to aid in effective cough & secretion clearance, in chronic bronchiectasis, CF, and bronchitis. Also by producing hyperinflation, nasal EPAP can improve cough and secretion clearance. Disorders such as bronchiectasis, cystic fibrosis (CF), and chronic bronchitis produce stagnant secretions. These can lead to acute purulent bronchitis or pneumonia, often due to resistant organisms such as *Pseudomonas*, which may have resulted from frequent antibiotic therapy. Respiratory devices, such as CPAP, PEP valves, acapella, flutter valves, and jet nebulizer aerosols, may be reduced or replaced. The nasal EPAP can also be used during exercise, in pulmonary emphysema, to decrease dyspnea and improve exercise capacity, by preventing bronchial collapse. Pulmonary Emphysema is a form of chronic obstructive pulmonary disease (COPD) characterized by dyspnea on exertion, due to dynamic hyperinflation. During exercise, this pathologic increase in FRC restricts the vital capacity (VC) and tidal volume (Vt) of the lungs. Work of breathing and breathlessness worsen, and exercise tolerance and functional capacity decline. Analogous to pursed-lip breathing, nasal EPAP worn during exercise stents the small airways during forced exhalation, preventing premature collapse. Work of breathing, dyspnea, and exercise capacity can improve.

Although a detailed description of a preferred embodiment of this disclosure has been shown and described hereinabove, it will be understood that various modifications and rearrangements of the parts and their respective features may be resorted to without departing from the scope of the disclosure as disclosed herein. One skilled in the art will recognize that other features can be included with the device or assembly of the present disclosure. For example, a compliance monitor of the type used in oral appliances can be incorporated into the present disclosure where the monitor/sensor detects motion and temperature. When incorporated into the device, the monitor provides an indication (e.g., wireless signal) of compliance of use by the patient.

The invention claimed is:

1. An expiratory positive airway pressure (EPAP) device comprising:
   a housing having an air flow path therethrough;
   at least one bi-resistance air flow assembly received in the air flow path that (i) allows air flow through the air flow path freely and without resistance upon inspiration, and (ii) allows air flow through the air flow path and produces a prescribed back pressure during expiration; and
   a bypass assembly that opens a bypass path at a predetermined level of back pressure during expiration;
   wherein the housing includes an air flow cartridge having a lumen and a flexible thin-walled shell that has a closed first end and an open second end;
   wherein the flexible thin-walled shell is oriented in the lumen whereby the flexible thin-walled shell expands upon expiration and seals along a substantial perimeter portion thereof with the lumen and produces the back pressure.

2. The EPAP device of claim 1, wherein the flexible thin-walled shell reduces a cross-sectional area of the air flow path during expiration.

3. The EPAP device of claim 2, wherein the flexible thin-walled shell is configured to seal the air flow path except along a predetermined portion.

4. The EPAP device of claim 2, wherein the flexible thin-walled shell collapses against the lumen on inspiration.

5. The EPAP device of claim 4, wherein the collapsed flexible thin-walled shell causes no fluidic resistance against inspiration.

6. The EPAP device of claim 3, wherein the bypass assembly includes a biasing member that closes the bypass path until the back pressure reaches the predetermined level.

7. The EPAP device of claim 1, wherein the flexible thin-walled shell is secured to the lumen over a portion of a surface of the flexible thin-walled shell.

8. The EPAP device of claim 7, wherein the lumen has a longitudinally extending groove adjacent to an un-secured portion of the flexible thin-walled shell.

9. The EPAP device of claim 8, wherein therapeutic resistive pressure is created by fluidic resistance of expiring air through the restricted cross-sectional area formed by the expanded flexible thin-walled shell and the groove of the cartridge.

10. The EPAP device of claim 8, which achieves clinically indicated positive airway pressure.

11. The EPAP device of claim 7, wherein the flexible thin-walled shell has an integral longitudinally extending rib that is adjacent to an un-secured portion of the flexible thin-walled shell.

12. The EPAP device of claim 1, further comprising nasal pillows that communicate with the air flow path and are configured for receipt in nares of an associated patient.

13. The EPAP device of claim 12 wherein the open end of the flexible thin-walled shell is closer than the closed end to the nasal pillows.

14. The EPAP device of claim 1, wherein the expanded flexible thin-walled shell forms a partial seal around the lumen of the cartridge except for an area created by a groove at least partially formed in a wall thickness of the cartridge.

15. The EPAP device of claim 1, wherein the air flow assembly is a cartridge that includes detachment members for easily attaching and detaching relative to the housing.

16. The EPAP device of claim 15, further comprising nasal pillows that include the detachment members for easily attaching and detaching relative to the housing.

17. The EPAP device of claim 16, wherein the cartridge is in series with the pillows along an associated patient's natural breathing flow path.

18. The EPAP device of claim 1, further comprising at least one strap for holding the device in position under a nose of an associated patient.

19. The EPAP device of claim 1, wherein the device is reusable and includes selectively detachable nasal pillows, air flow assembly cartridges, and a headgear retention mechanism that are intended to be replaceable.

* * * * *